(12) United States Patent
Fukazawa et al.

(10) Patent No.: US 8,705,034 B2
(45) Date of Patent: *Apr. 22, 2014

(54) EVALUATION DEVICE AND EVALUATION METHOD

(71) Applicant: Nikon Corporation, Tokyo (JP)

(72) Inventors: Kazuhiko Fukazawa, Kamakura (JP); Yuji Kudo, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,686

(22) Filed: Nov. 14, 2012

(65) Prior Publication Data

US 2013/0070244 A1 Mar. 21, 2013

Related U.S. Application Data

(60) Division of application No. 13/067,101, filed on May 9, 2011, now Pat. No. 8,334,977, which is a continuation of application No. PCT/JP2009/005964, filed on Nov. 9, 2008.

(30) Foreign Application Priority Data

Nov. 10, 2008 (JP) ................................. 2008-287503

(51) Int. Cl.
*G01J 4/00* (2006.01)
(52) U.S. Cl.
USPC .......................................................... 356/369
(58) Field of Classification Search
USPC ....................................... 356/364–369, 237.1
See application file for complete search history.

(56) References Cited

U.S. PATENT DOCUMENTS

| | | | |
|---|---|---|---|
| 5,877,859 A | 3/1999 | Aspnes et al. | |
| 6,597,463 B1 | 7/2003 | Singh et al. | |
| 6,774,987 B2 | 8/2004 | Komatsu et al. | |
| 7,586,607 B2 | 9/2009 | Sun | |
| 7,692,780 B2 | 4/2010 | Oomori et al. | |
| 7,889,339 B1 | 2/2011 | Flock et al. | |
| 7,907,268 B2 | 3/2011 | Fujimori et al. | |
| 2002/0067477 A1* | 6/2002 | Morita et al. | 356/237.5 |
| 2006/0098189 A1 | 5/2006 | Oomori et al. | |

(Continued)

FOREIGN PATENT DOCUMENTS

| | | |
|---|---|---|
| JP | 2006-135211 | 5/2006 |
| JP | 2006-250843 | 9/2006 |

(Continued)

OTHER PUBLICATIONS

International Search Report for PCT/JP2009/005964, mailed Feb. 16, 2010.

(Continued)

*Primary Examiner* — Kara E Geisel
(74) *Attorney, Agent, or Firm* — Staas & Halsey LLP

(57) ABSTRACT

In an evaluation device, an analyzer is rotated so that the azimuth of the transmission axis of the analyzer has an inclination angle of 90 degrees±3 degrees with respect to the transmission axis of a polarizer. An imaging camera captures a regularly reflected image of a wafer under each condition, and an image processing unit evaluates the shape of a repeating pattern and detects dose defects and focus defects on the basis of the two images of the wafer captured by the imaging camera.

19 Claims, 12 Drawing Sheets

(56) References Cited

U.S. PATENT DOCUMENTS

| | | |
|---|---|---|
| 2009/0079983 A1 | 3/2009 | Fujimori et al. |
| 2010/0177312 A1 | 7/2010 | Fujimori et al. |
| 2010/0182603 A1 | 7/2010 | Fujimori et al. |

FOREIGN PATENT DOCUMENTS

| | | |
|---|---|---|
| JP | 2007-303903 | 11/2007 |
| JP | 2007-304062 | 11/2007 |
| JP | 2007-309874 | 11/2007 |
| JP | 2007-327796 | 12/2007 |

OTHER PUBLICATIONS

U.S. Office Action mailed Dec. 22, 2011 in related U.S. Appl. No. 13/067,101.

U.S. Notice of Allowance mailed Aug. 16, 2010 in related U.S. Appl. No. 13/067,101.

U.S. Appl. No. 13/067,101, filed May 9, 2001, Kazuhiko Fukazawa et al., Nikon Corporation Toyko, Japan.

* cited by examiner

DEFICIENT EXPOSURE ← CORRECT EXPOSURE → EXCESSIVE EXPOSURE

FOCUS MINUS ← FOCUS NORMAL → FOCUS PLUS

INCIDENT LINEARLY POLARIZED LIGHT

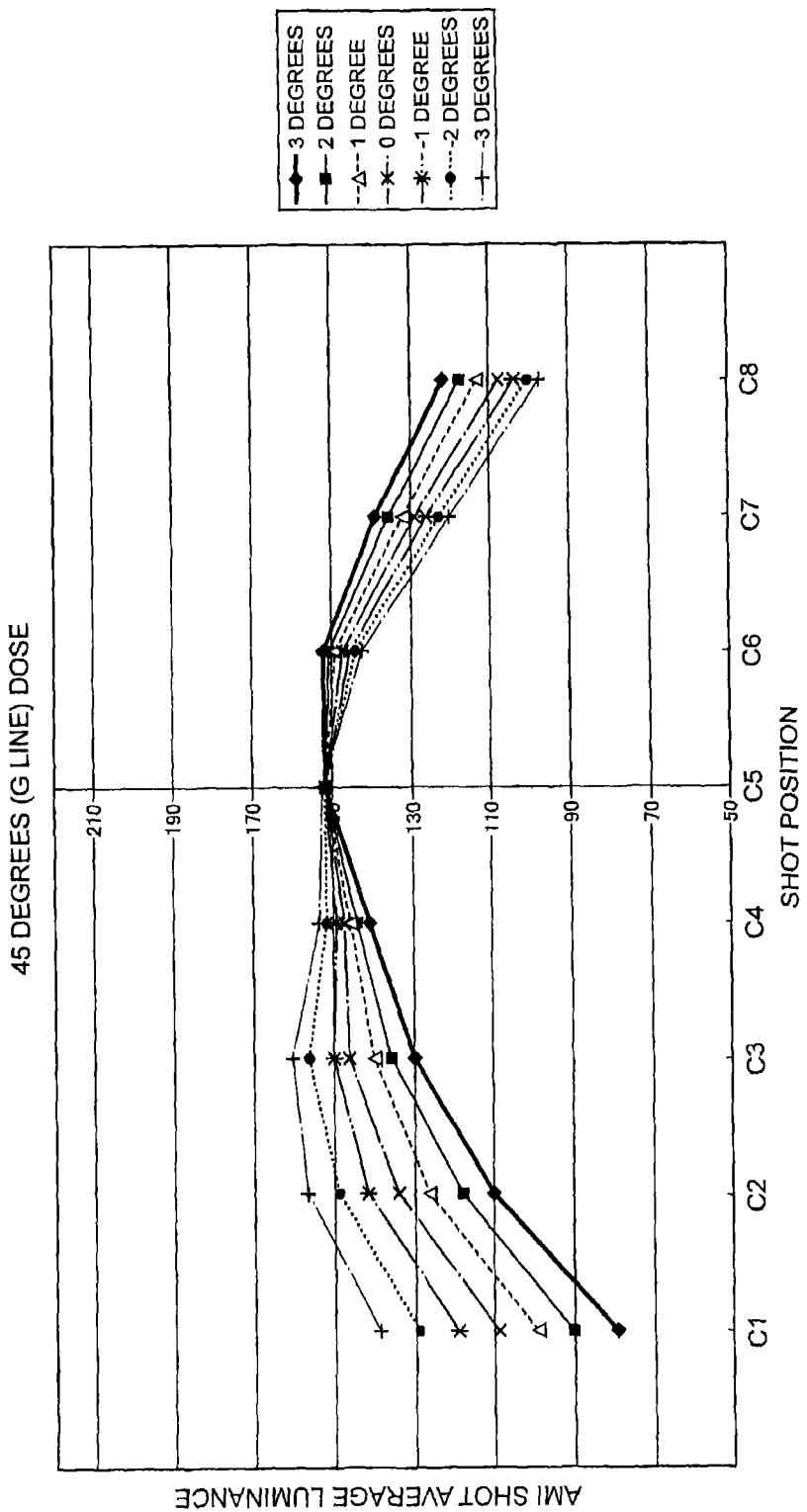

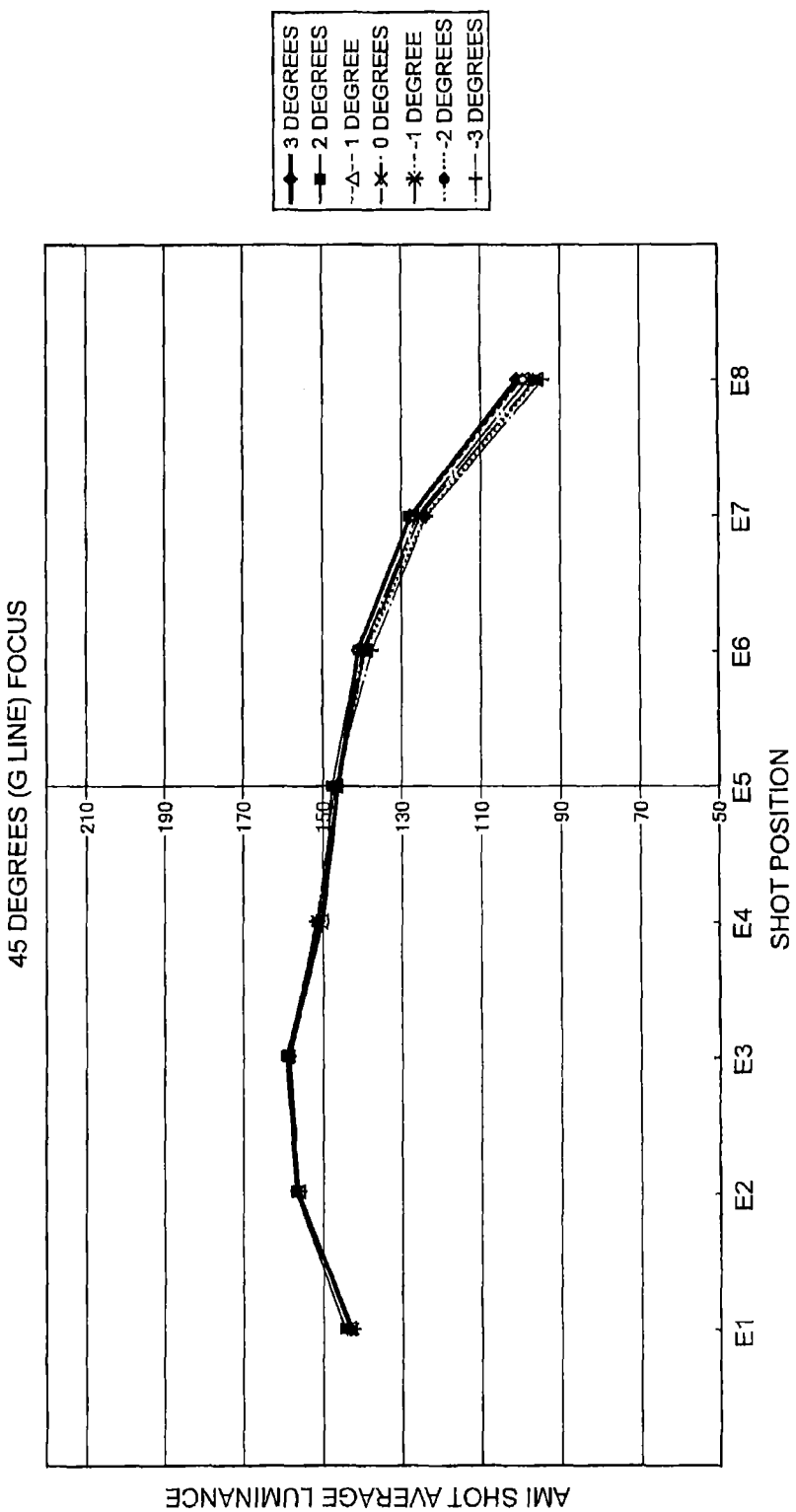

US 8,705,034 B2

EVALUATION DEVICE AND EVALUATION METHOD

This is a divisional of co-pending U.S. Ser. No. 13/067,101 filed on May 9, 2011 which is a continuation of PCT International Application No. PCT/JP2009/005964, filed on Nov. 9, 2009, both of which are hereby incorporated by reference. This application also claims the benefit of Japanese Patent Application No. 2008-287503, filed in Japan on Nov. 10, 2008, which is hereby incorporated by reference.

TECHNICAL FIELD

The present invention relates to an evaluation device and evaluation method for evaluating a pattern formed on the surface of a semiconductor wafer, a liquid crystal substrate, or the like.

TECHNICAL BACKGROUND

Various methods for measuring a cross-sectional shape by scanning electron microscope (SEM) viewing have been proposed as methods for determining the quality of a pattern formed on the surface of a semiconductor wafer. Measurement of a cross-sectional shape by SEM is performed by a method in which an electron beam radiated to a pattern on the tested substrate is scanned in the cross-sectional direction of the pattern, reflected electrons or secondary electrons from the pattern are detected and analyzed, and the cross-sectional shape of the scanned portion is calculated. The operation described above is performed at several points on the pattern to determine the quality of the shape of the entire pattern.

In measurement by SEM as described above, the operation of radiating and scanning an electron beam on the pattern is repeated several times, and a long time is therefore required to calculate the shape of the pattern. Since the viewing magnification is also high, the pattern shape for the entire wafer is difficult to calculate, and the quality of the entire wafer is determined by sampling several points. As a result, flaws in portions of the pattern other than those sampled are overlooked. In a resist pattern, when an electron beam is radiated, the electron beam is absorbed by the resist according to the acceleration voltage, and the pattern becomes charged and eroded. In some cases, discharge occurs and the pattern collapses, and because of inconvenience in subsequent steps, the optimum viewing conditions are also calculated while various modifications are made to the acceleration voltage or the viewing magnification. Measurement therefore requires even more time.

In order to overcome such problems, a surface inspection device and surface inspection method have been proposed whereby the quality of a pattern shape on a tested substrate can be distinguished in a short time regardless of whether the pattern is a resist pattern or an etched pattern (see Japanese Laid-open Publication No. 2006-135211, for example).

SUMMARY OF THE INVENTION

Problems To Be Solved By the Invention

However, in methods such as the one described above, dose defects and focus defects cannot be distinguished, and the cause of an abnormality in the pattern cannot be specified.

The evaluation device of the present invention for achieving the aforementioned object comprises an illumination unit for radiating linearly polarized light to a surface of a substrate having a predetermined repeating pattern; an analyzer for extracting a polarization component having a different direction of vibration than the linearly polarized light from among regularly reflected light from the repeating pattern irradiated by the linearly polarized light; an imaging unit for capturing a regularly reflected image of the substrate based on the polarization component extracted by the analyzer; a setting unit for setting an angle condition between the direction of vibration of the linearly polarized light and the direction of vibration of the polarization component, or between the direction of vibration of the linearly polarized light and the direction of repetition of the repeating pattern; and an evaluation unit for evaluating a state of the repeating pattern on the basis of an image of the regularly reflected image captured by the imaging unit; the imaging unit being configured so as to capture the regularly reflected image obtained in a plurality of angle conditions between the direction of vibration of the linearly polarized light and the direction of vibration of the polarization component, or a plurality of angle conditions between the direction of vibration of the linearly polarized light and the direction of repetition of the repeating pattern, the angle conditions being set by the setting unit; and the evaluation unit being configured so as to evaluate a state of the repeating pattern on the basis of images of the plurality of regularly reflected images captured by the imaging unit.

BRIEF DESCRIPTION OF THE DRAWINGS

FIG. 10 is a view showing the relationship between the average luminance and the dose variation for each shot in a difference image;

FIG. 11 is a view showing the relationship between the average luminance and the focus variation for each shot in an average image;

DESCRIPTION OF THE EMBODIMENTS

Embodiments of the present invention will be described below with reference to the accompanying drawings. The evaluation device 1 of the present embodiment is provided with a stage 20 for supporting a semiconductor wafer 10

Figure 1:
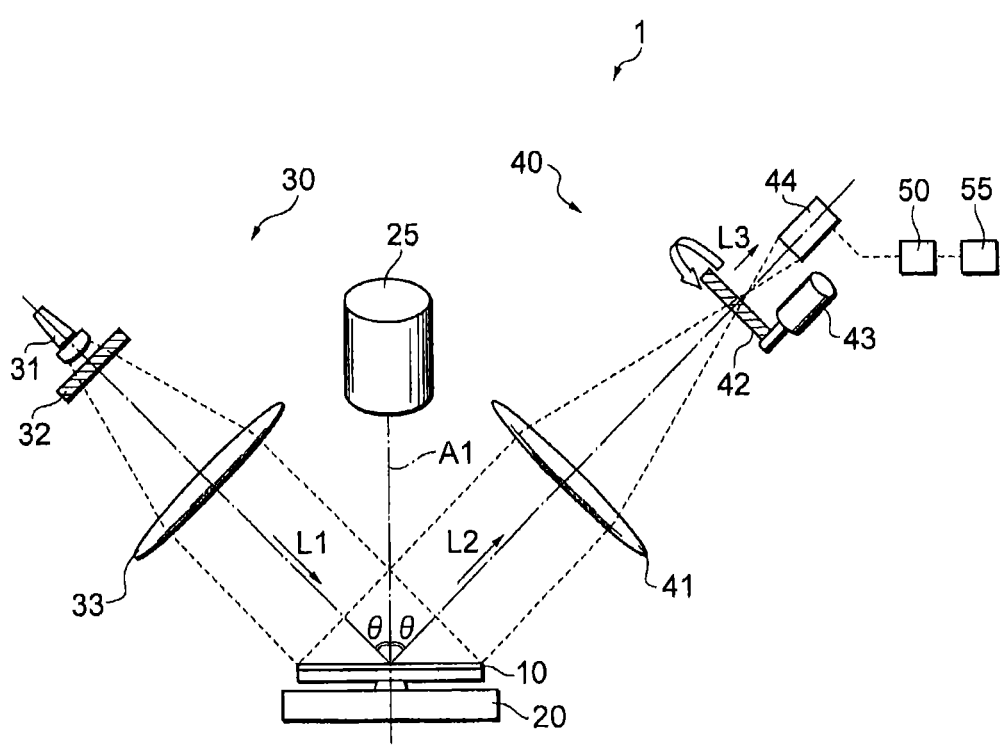
FIG. 1 is a view showing the overall configuration of the evaluation device.

(hereinafter referred to as a wafer 10), an alignment system 25, an illumination system 30, and an acceptance system 40, as shown in FIG. 1. The evaluation device 1 is also provided with an image processing unit 50 for performing image processing of an image captured by the acceptance system 40, and a monitor 55 for displaying the image captured by the acceptance system 40 or an image processing result obtained by the image processing unit 50. After exposure/development of a resist film of a top layer by an exposure device, the wafer 10 is carried from the development device or a wafer cassette not shown in the drawing by a conveyance system not shown in the drawing, and is suction-retained on the stage 20.

Figure 2:
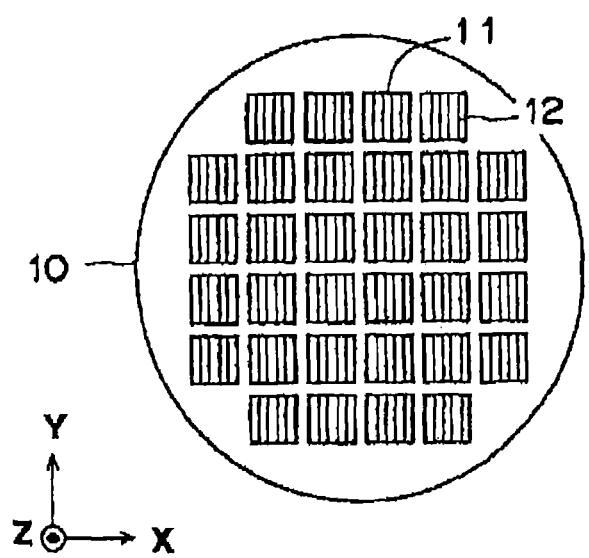
FIG. 2 is an external view of the surface of a semiconductor wafer.
Figure 3:
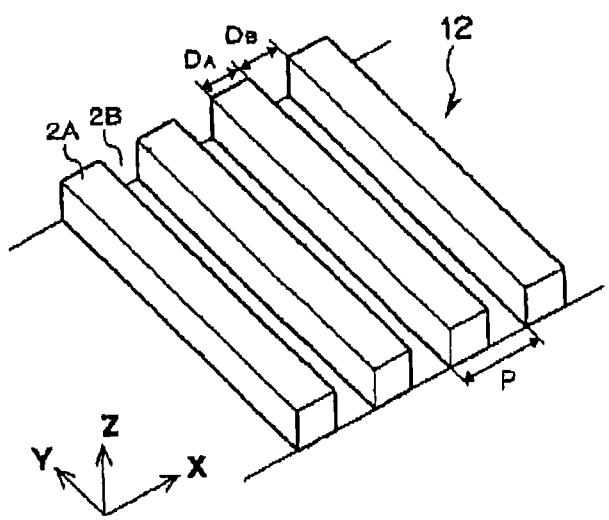
FIG. 3 is a perspective view showing the groove/ridge structure of the repeating pattern.

As shown in FIG. 2, a plurality of chip regions 11 is arranged in XY directions on a surface of the wafer 10, and a predetermined repeating pattern 12 is formed in each chip region. As shown in FIG. 3, the repeating pattern 12 is a resist pattern (e.g., wiring pattern) in which a plurality of line portions 2A is arranged at a constant pitch P in the minor-axis direction (X direction). The spaces between adjacent line portions 2A are space portions 2B. The arrangement direction (X direction) of the line portions 2A is referred to as the "direction of repetition of the repeating pattern 12."

The design value of the line width $D_A$ of each line portion 2A in the repeating pattern 12 is ½ the pitch P. In a case in which the repeating pattern 12 is formed in accordance with the design value, the line width $D_A$ of each line portion 2A and the line width $D_B$ of each space portion 2B are equal, and the volume ratio of the line portions 2A and the space portions 2B is substantially 1:1. In contrast, when the exposure dose during formation of the repeating pattern 12 is not the correct value, although the pitch P does not change, the line width $D_A$ of the line portions 2A differs from the design value, as does also the line width $D_B$ of the space portions 2B, and the volume ratio of the line portions 2A and space portions 2B deviates from substantially 1:1.

The evaluation device 1 of the present embodiment utilizes the variation in the volume ratio of the line portions 2A and space portions 2B in the repeating pattern 12 such as described above to evaluate the shape of the repeating pattern 12. An ideal volume ratio (design value) of 1:1 will be used to simplify the description. The variation in the volume ratio is caused by deviation of the exposure dose from the correct state, and occurs at each shot region of the wafer 10. The volume ratio can also be described as the area ratio of a cross-sectional shape.

In the present embodiment, the pitch P of the repeating pattern 12 is set so as to be adequately small in relation to the wavelength of the illumination light (described hereinafter) on the repeating pattern 12. For example, when H-line (wavelength λ=405 nm) illumination light is used on a pattern having a half pitch of 70 nm, the pitch is ½ or less of the wavelength of the illumination light, and diffracted light is not generated. Diffracted light thus does is not generated from the repeating pattern 12, and the shape of the repeating pattern 12 cannot be evaluated by diffracted light.

The stage 20 of the evaluation device 1 supports the wafer 10 on the upper surface thereof, and fixes the wafer 10 in place by vacuum suction, for example. The stage 20 is also capable of rotating about a normal line A1 as a central axis at the center of the upper surface thereof. Through this rotation mechanism, the direction of repetition (X direction in FIGS. 2 and 3) of the repeating pattern 12 in the wafer 10 can be rotated in the surface of the wafer 10. The upper surface of the stage 20 is in the horizontal plane, and the stage 20 can keep the wafer 10 always in a horizontal state.

The alignment system 25 illuminates an outer edge part of the wafer 10, detects the position of an outline reference (e.g., notch) provided to the outer edge part in the rotation direction, and stops the stage 20 at a predetermined position. As a result, the direction of repetition (X direction in FIGS. 2 and 3) of the repeating pattern 12 in the wafer 10 can be set so as to be inclined 45 degrees with respect to an incident plane A2 (see FIG. 4) of the illumination light described hereinafter. The angle is also not limited to 45 degrees, and can be set to 22.5 degrees, 67.5 degrees, or any other angle direction.

The illumination system 30 is a decentered optical system composed of a light source 31, a polarizer 32, and an illumination lens 33, and illuminates the repeating pattern 12 of the wafer 10 on the stage 20 through the use of linearly polarized light L1 (first linearly polarized light). The linearly polarized light L1 is the illumination light for the repeating pattern 12. The linearly polarized light L1 is radiated to the entire surface of the wafer 10.

Figure 4:
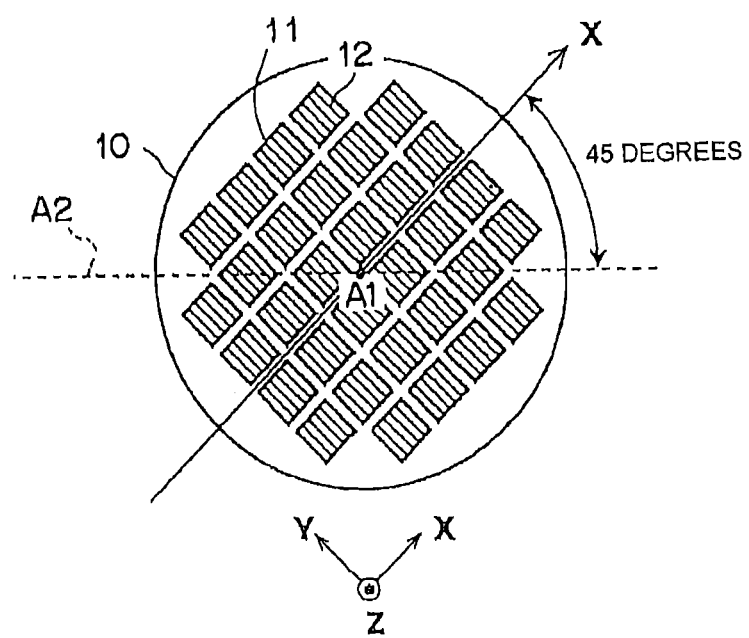
FIG. 4 is a view showing the state of inclination between the incident plane of the linearly polarized light and the direction of repetition of the repeating pattern.

The propagation direction of the linearly polarized light L1 (direction of the principal ray of the linearly polarized light L1 that reaches an arbitrary point on the surface of the wafer 10) passes through the center of the stage 20 and is inclined at a predetermined angle θ with respect to the normal line A1 of the stage 20. Incidentally, the plane parallel to the normal line A1 of the stage 20 and including the propagation direction of the linearly polarized light L1 is the incident plane of the linearly polarized light L1. The incident plane A2 in FIG. 4 is the incident plane in the center of the wafer 10.

In the present embodiment, the linearly polarized light L1 is p-polarized light. The plane of vibration of the linearly polarized light L1 is specified by the transmission axis of the polarizer 32.

The light source 31 of the illumination system 30 is an inexpensive discharge light source or an LED The polarizer 32 is disposed in the vicinity of the emission end of the light source 31, the transmission axis thereof is set to a predetermined azimuth, and the light from the light source 31 is converted to linearly polarized light L1 in accordance with the transmission axis. The front focal point of illumination lens 33 substantially coincides with the emission end of the light source 31, is disposed so that the back focal point substantially coincides with the surface of the wafer 10, and guides the light from the polarizer 32 to the surface of the wafer 10. In other words, the illumination system 30 is a telecentric optical system with respect to the wafer 10 side.

In the illumination system 30 described above, the light from the light source 31 is converted to p-polarized linearly polarized light L1 via the polarizer 32 and the illumination lens 33, and is incident on the entire surface of the wafer 10. The incident angle of the linearly polarized light L1, being composed of parallel luminous fluxes, is the same at each point of the wafer 10, and corresponds to the angle θ formed by the optical axis and the normal line A1.

Figure 5:
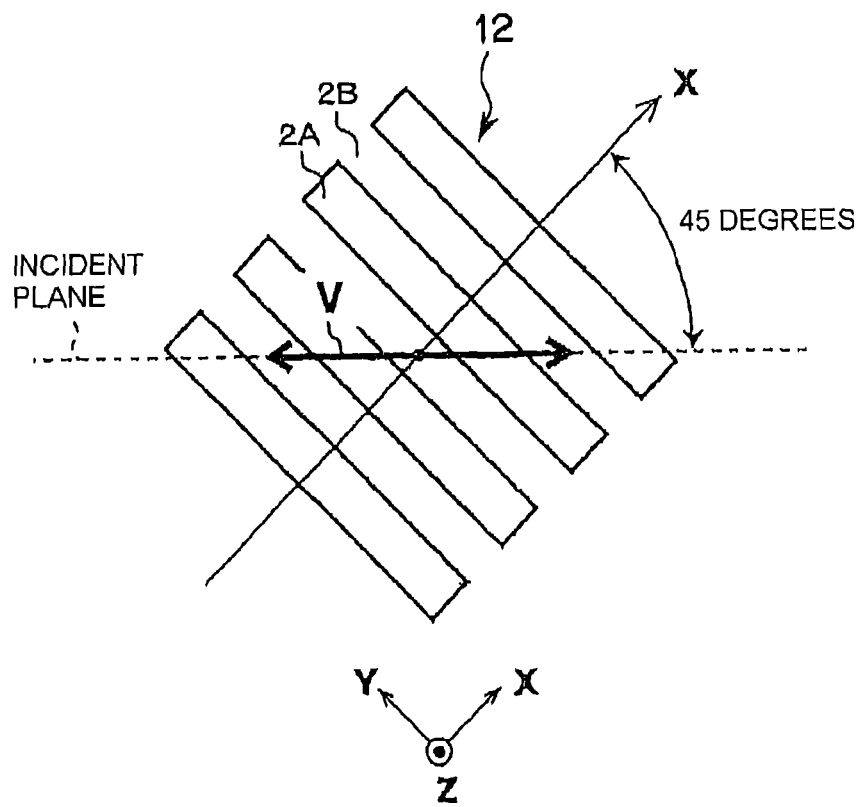
FIG. 5 is a view showing the state of inclination between the direction of the plane of vibration of the linearly polarized light and the direction of repetition of the repeating pattern.

In the present embodiment, since the linearly polarized light L1 incident on the wafer 10 is p-polarized light, in a case in which the direction of repetition (X direction) of the repeating pattern 12 is set to an angle of 45 degrees with respect to the incident plane A2 (propagation direction of the linearly polarized light L1 at the surface of the wafer 10) of the linearly polarized light L1, as shown in FIG. 4, the angle formed by the direction of the plane of vibration (V direction in FIG. 5) of the linearly polarized light L1 at the surface of the wafer 10 and the direction of repetition (X direction) of the repeating pattern 12 is also set to 45 degrees.

In other words, the linearly polarized light L1 is incident on the repeating pattern 12 so as to traverse the repeating pattern 12 at an angle in a state in which the direction of the plane of vibration (V direction in FIG. 5) of the linearly polarized light L1 at the surface of the wafer 10 is inclined 45 degrees with respect to the direction of repetition (X direction) of the repeating pattern 12.

The angle state of the linearly polarized light L1 and the repeating pattern 12 such as described above is uniform for the entire surface of the wafer 10. The angle formed by the direction of the plane of vibration (V direction) in FIG. 5 and the direction of repetition (X direction) is set to 45 degrees in order to maximize the variation of the polarization state by the repeating pattern 12.

When the linearly polarized light L1 described above is used to illuminate the repeating pattern 12, elliptically polarized light L2 is generated in the regular reflection direction from the repeating pattern 12. In this case, the propagation direction of the elliptically polarized light L2 coincides with the regular reflection direction. The regular reflection direction is included within the incident plane A2 of the linearly polarized light L1, and is a direction inclined at an angle θ (an angle equal to the incident angle θ of the linearly polarized light L1) to the opposite side from the incident direction with respect to the normal line A1 of the stage 20. As described above, since the pitch P of the repeating pattern 12 is adequately short in relation to the illumination wavelength, no diffracted light is generated from the repeating pattern 12.

As shown in FIG. 1, the acceptance system 40 is composed of an acceptance lens 41, an analyzer 42, a rotation drive device 43, and an imaging camera 44. The optical axis of the acceptance system 40 passes through the center of the stage 20, and is inclined at an angle θ with respect to the normal line A1 of the stage 20. The acceptance lens 41 collects the elliptically polarized light L2 at an imaging surface of the imaging camera 44.

The analyzer 42 is configured so that the azimuth (polarization direction) of the transmission axis can be rotated about the optical axis of the acceptance system 40, through the use of the rotation drive device 43, and the azimuth of the transmission axis of the analyzer 42 is set so as to be inclined at an inclination angle 90 degrees forward or backward with respect to the transmission axis of the polarizer 32 described above. In other words, a crossed-Nicols state can be deliberately eliminated. When the elliptically polarized light L2 passes through the analyzer 42, second linearly polarized light L3 is collected on the imaging surface of the imaging camera 44, the second linearly polarized light L3 being a polarization component whose direction of vibration is at substantially a right angle with respect to the direction of vibration of the linearly polarized light L1 among the elliptically polarized light L2 which is regularly reflected light from the surface of the wafer 10. As a result, a regularly reflected image of the wafer 10 is formed by the second linearly polarized light L3 on the imaging surface of the imaging camera 44.

The imaging camera 44 is a CCD camera having a CCD picture device not shown in the drawing, and the imaging camera 44 photoelectrically converts the regularly reflected image of the wafer 10 formed on the imaging surface and outputs an image signal to the image processing unit 50. The brightness of the regularly reflected image of the wafer 10 is substantially proportional to the light intensity of the linearly polarized light L3 and varies according to the shape of the repeating pattern 12. The regularly reflected image of the wafer 10 is brightest when the repeating pattern 12 is the ideal shape. A brightness of the regularly reflected image of the wafer 10 occurs for each shot region.

The image processing unit 50 converts the image of the wafer 10 (regularly reflected image) to a digital image having a predetermined bit number (e.g., 8-bit) on the basis of an image signal of the wafer 10 inputted from the imaging camera 44. The image processing unit 50 also performs predetermined image processing of the image of the wafer 10 and evaluates the shape of the repeating pattern 12. The evaluation result of the image processing unit 50 for the repeating pattern 12, and the image of the wafer 10 at that time, are outputted and displayed by the monitor 55.

Figure 6:
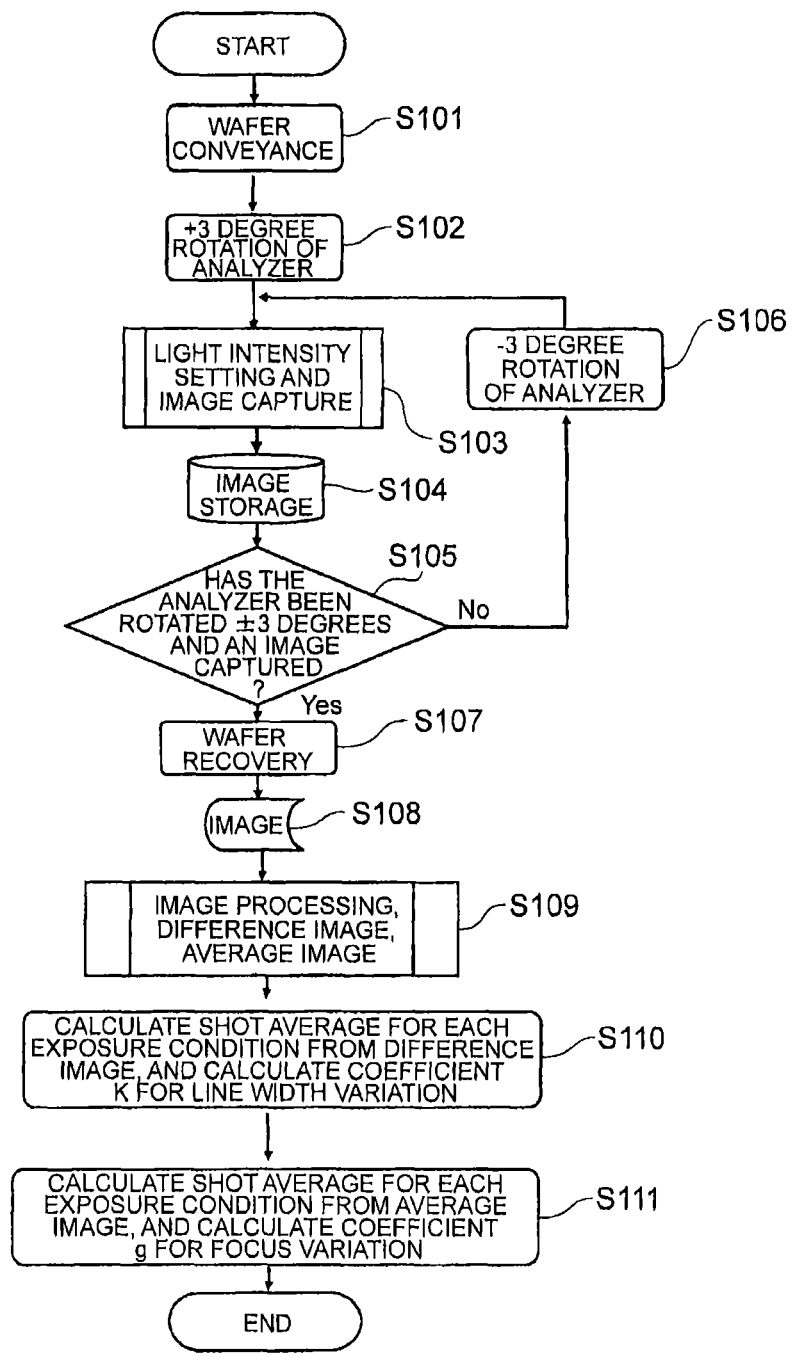
FIG. 6 is a flowchart showing the recipe creation method.

The method for evaluating the repeating pattern 12 by using the evaluation device 1 of the present embodiment will be described with reference to the flowcharts shown in FIGS. 6 and 7. A recipe creation operation is first performed before evaluation of the repeating pattern 12 (see FIG. 6). The reason for performing this operation is that conditions for performing the optimum evaluation must be determined in the evaluation of the repeating pattern 12. Therefore, a wafer which is exposed and developed under conditions in which the focus (amount of misalignment of the focus position from the correct focus state) and the dose (exposure amount) of an exposure machine are allocated (varied) for each shot in advance is first conveyed to the stage 20 (step S101).

The condition-allocated wafer (not shown) such as described above is created so that there exists a best shot (non-defective shot) through optimum focus and dose as a reference. The wafer at this time is not limited to being a condition-allocated wafer, and may be a wafer in which there is a flaw due to omission. After the condition-allocated wafer is conveyed, an alignment is performed so that the direction of repetition of the repeating pattern is inclined 45 degrees with respect to the illumination direction (propagation direction of the linearly polarized light L1 at the surface of the wafer 10). The angle of the alignment is not limited to 45 degrees, and may be 67.5 degrees or 22.5 degrees.

As described above, the analyzer 42 is configured so that the azimuth (polarization direction) of the transmission axis thereof can be rotated by using the rotation drive device 43, and after conveyance and alignment of the condition-allocated wafer (not shown), the analyzer 42 is rotated so that the azimuth of the transmission axis of the analyzer 42 has an inclination angle of 90 degrees+3 degrees (93 degrees) with respect to the transmission axis of the polarizer 32 (step S102). At this time, the angle formed by the direction of vibration in the plane perpendicular to the propagation direction of the linearly polarized light L1, and the direction of vibration in the plane perpendicular to the propagation direction of the second linearly polarized light L3, is set to 90 degrees+3 degrees (93 degrees).

The linearly polarized light L1 is then radiated to the surface of the condition-allocated wafer (not shown), and the regularly reflected light (elliptically polarized light L2) reflected by the surface of the condition-allocated wafer is detected and captured by the imaging camera 44 via the analyzer 42 (step S103). At this time, the light from the light source 31 is converted to linearly polarized light L1 via the polarizer 32 and the illumination lens 33 and radiated to the surface of the condition-allocated wafer. The regularly reflected light (elliptically polarized light L2) reflected by the surface of the condition-allocated wafer is collected by the acceptance lens 41, the second linearly polarized light L3 is extracted by the analyzer 42 to form an image on the imaging surface of the imaging camera 44, and the imaging camera 44 photoelectrically converts the regularly reflected image of the condition-allocated wafer formed on the imaging surface by the second linearly polarized light L3, generates an image signal, and outputs the image signal to the image processing unit 50.

When the image signal of the condition-allocated wafer produced from the second linearly polarized light L3 is inputted to the image processing unit 50, the image signal is stored in an internal memory (not shown) of the image processing unit 50 (step S104).

A determination is then made as to whether the analyzer 42 has been rotated so that the azimuth of the transmission axis of the analyzer 42 has an inclination angle of 90 degrees±3 degrees with respect to the transmission axis of the polarizer 32, and the regularly reflected image of the condition-allocated wafer has been captured under each condition (step S105). In a case in which the determination is "No," the process proceeds to step S106, and after the analyzer 42 is rotated so that the azimuth of the transmission axis of the analyzer 42 has an inclination angle of 90 degrees−3 degrees (87 degrees) with respect to the transmission axis of the polarizer 32, the imaging of step S103 and the image storage of step S104 are repeated, and the process returns to step S105. At this time, the angle formed by the direction of vibration in the plane perpendicular to the propagation direction of the linearly polarized light L1, and the direction of vibration in the plane perpendicular to the propagation direction of the second linearly polarized light L3 is set to 90 degrees−3 degrees (87 degrees).

At this time, the brightness of the captured reference shot (best non-defective shot) portion must be constant regardless of the state of the analyzer 42. In order to achieve this, the wafer is photographed at an illumination intensity having an initial value after setting of the analyzer 42 is ended, the image is sent to the image processing unit 50, and the luminance of the reference shot (best non-defective shot) portion is calculated by 256 gradations, for example, by the image processing unit 50. When the luminance of the reference shot (best non-defective shot) portion is 120 gradations (within the 256 gradations), the illumination intensity thereof is stored as the illumination intensity of the state of the analyzer 42. In a case in which the luminance of the reference shot (best non-defective shot) portion in the obtained image is not 120 gradations, the illumination intensity is adjusted by an ND filter or the like not shown in the drawing, the condition is calculated for which the luminance of the reference shot (best non-defective shot) portion is 120 gradations, and the obtained illumination intensity condition is correlated with the state of the analyzer 42 and stored. The luminance of the reference shot (best non-defective shot) position is thus calculated from the captured image, and the amount of illumination light is adjusted each time to achieve a constant luminance. Two images are thereby stored having the same luminance value of the reference shot and different azimuths of the transmission axis of the analyzer 42.

In a case in which the determination in step S105 is "Yes," the process proceeds to step S107, and the condition-allocated wafer (not shown) is recovered. Although a larger rotation angle range of the analyzer 42 produces a larger amount of luminance variation in a defective shot, since the noise component (other than the amount of polarization variation) increases, a range of ±3 degrees to ±5 degrees is preferred.

When the condition-allocated wafer is recovered, the image processing unit 50 reads the two images acquired in the previous step from the internal memory (step S108), and uses image processing to calculate images (hereinafter referred to as a difference image and an average image) which are based on a difference and average of the signal strength in the two read images (step S109). In order to calculate a difference image, the difference of the signal strength in the two images is calculated in pixel units, and the difference image is generated with the difference value calculated in pixel units as the signal strength. In order to calculate an average image, the average of the signal strength in the two images is calculated in pixel units, and the average image is generated with the average value calculated in pixel units as the signal strength.

When the difference image and average image are calculated, the calculated difference image is used to compute the average value (i.e., the average value of the difference of the signal strength (luminance) in the two images) of the luminance (signal strength) for each shot in which the dose (exposure amount) is varied, and a coefficient K is calculated for calculating the variation (hereinafter referred to as line width variation) of the width of the line portions 2A caused by the variation of the dose (step S110). The dose luminance variation caused by the variation of the dose herein is equal to the difference of the signal strength (luminance) in the two images, and can be expressed by the following equations (1) and (2), where ±α is the rotation angle range of the analyzer 42.

$$\text{Dose luminance variation} = (+\alpha \text{ image luminance}) - (-\alpha \text{ image luminance}) \quad (1)$$

$$\text{Dose luminance variation} = (-\alpha \text{ image luminance}) - (+\alpha \text{ image luminance}) \quad (2)$$

A correlation such as indicated by Equation (3) below exists between the line width variation and the dose luminance variation.

$$\text{Line width variation} = K \times \text{Dose luminance variation} \quad (3)$$

Figure 8B:
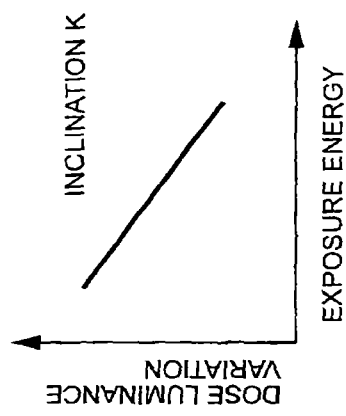
FIG. 8B is a graph showing the relationship between the dose luminance variation and the exposure energy amount.
Figure 8A:
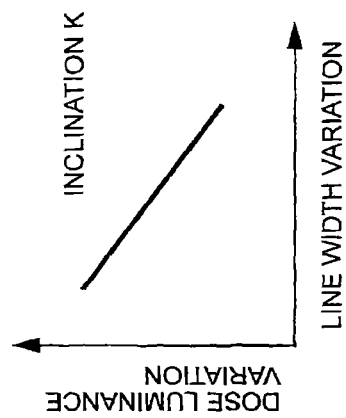
FIG. 8A is a graph showing the relationship between the dose luminance variation and the line width variation.

Therefore, the coefficient K can be calculated from the difference (dose luminance variation) of the signal strength (luminance) and the measured value of the line width by measuring the line width (width of the line portions 2A) in advance for each shot in which the dose is varied using scanning electron microscope (SEM) measurement or scatterometry measurement. When the repeating pattern 12 is evaluated, the line width variation (i.e., the shape variation of the repeating pattern 12) caused by variation of the dose (exposure amount) can be detected from the difference (dose luminance variation) of the signal strength (luminance), by using the calculated coefficient K in Equation (3). The relationship between the dose luminance variation and the line width variation is shown in FIG. 8A.

A correlation between the dose (exposure energy amount) and the luminance variation (dose luminance variation), such as the one indicated by Equation (4), may also be used.

$$\text{Exposure energy amount} = K \times \text{Dose luminance variation} \quad (4)$$

In this case, by calculating the dose (exposure energy amount) in advance for each shot from the setting of the exposure device (not shown), the coefficient K can be calculated from the exposure energy amount and the difference (dose luminance variation) of the signal strength (luminance). When the repeating pattern 12 is evaluated, the variation (i.e., the shape variation of the repeating pattern 12) of the dose (exposure amount) can be detected from the difference (dose luminance variation) of the signal strength (luminance) by using the calculated coefficient K in Equation (4). The relationship between the dose luminance variation and the exposure energy amount is shown in FIG. 8B.

The computed average image is then used to compute the average value (i.e., the average value of the average of the signal strength (luminance) in the two images) of the luminance (signal strength) for each shot in which the focus is varied, a coefficient g for calculating the focus variation amount is calculated, and the recipe creation operation is ended (step S111). The luminance variation (focus luminance variation) caused by misalignment of the focus can be expressed by Equation (5) below.

Focus luminance variation={(+α image luminance)+
(−α image luminance)}/2−f(Line width variation)  (5)

In the equation above, f is a "luminance variation according to line width variation" function. When g is a "focus luminance variation according to focus variation amount" function, the focus variation amount and the focus luminance variation are related to each other as indicated by Equation (6) below.

Focus variation amount=$g^{-1}$(focus luminance variation)  (6)

Therefore, by calculating the focus variation amount (focus offset value) in advance for each shot from the setting of the exposure device (not shown), the functions f and g can be calculated from the focus variation amount and the signal strength (luminance) of the average image. When the repeating pattern 12 is evaluated, the variation (i.e., the shape variation of the repeating pattern 12) of the focus can be detected from the signal strength (luminance) of the average image by using the calculated function f in Equation (5) and using the calculated function g in Equation (6).

Figure 9A:
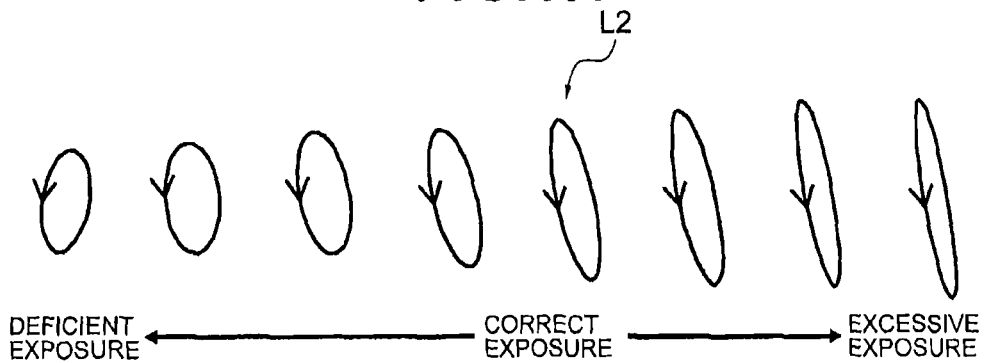
FIGS. 9A and 9B are views showing the polarization state of the elliptically polarized light reflected from each shot of a condition-allocated wafer.
Figure 9B:
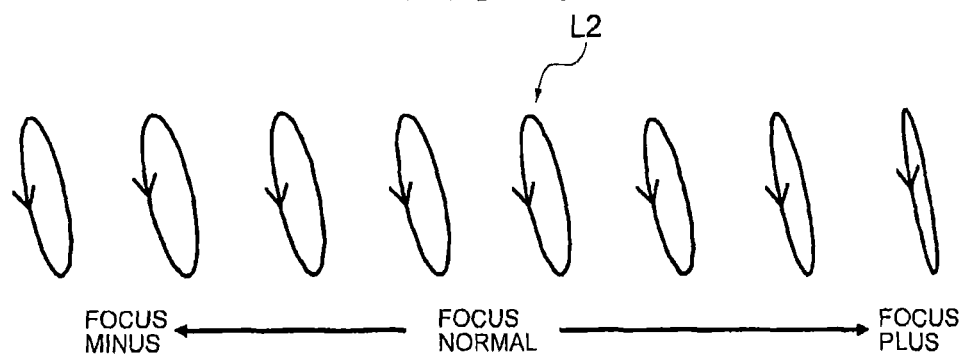
Figure 9C:
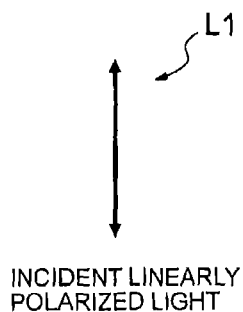
FIG. 9C is a view showing the polarization state of the linearly polarized light.

The reason that dose defects and focus defects can be distinguished and detected will next be described. FIG. 9 is a view showing the polarization state of the elliptically polarized light L2 that is reflected from each shot of the condition-allocated wafer (not shown). In FIG. 9A, polarization states are shown in which the exposure amount (dose) in each shot is deliberately excessive or deficient, the correct exposure amount is near the center of FIG. 9A, the exposure amount becomes more deficient in the shot the further to the left in FIG. 9A, and the exposure amount becomes more excessive in the shot the further to the right in FIG. 9A. When a pattern having form birefringence is illuminated by linearly polarized light L1 such as shown in FIG. 9C, the reflected light is generally elliptically polarized light L2 which is inclined. It is apparent from FIG. 9A that when the exposure amount is varied, the fatness of the elliptically polarized light L2 varies, and the angle and length of the major axis of the ellipse vary. In FIG. 9B, polarization states are shown in which the focus in each shot is deliberately varied, the correct focus is near the center of FIG. 9B, the focus in the shot is more to the minus side the further to the left in FIG. 9B, and the focus in the shot is more to the plus side the further to the right in FIG. 9B. It is apparent from FIG. 9B that when the focus is varied, although the fatness of the elliptically polarized light L2 varies, the angle and length of the major axis of the ellipse are virtually unchanged.

Therefore, when the analyzer 42 is rotated so that the azimuth of the transmission axis of the analyzer 42 has an inclination angle of 90 degrees±3 degrees with respect to the transmission axis of the polarizer 32, and the two images of the wafer captured under each condition are compared as described above, there is no variation or an extremely small variation in the brightness of the two images (shots) even when there is a focus defect, and the brightness of the two images (shots) varies when there is a dose defect. Even when the analyzer 42 is rotated so that the azimuth of the transmission axis of the analyzer 42 has an inclination angle other than 90 degrees±3 degrees (e.g., 90 degrees ±1 degree or 2 degrees) with respect to the transmission axis of the polarizer 32, there is no variation or an extremely small variation in the brightness of the two images (shots) even when there is a focus defect, and the brightness of the two images (shots) varies when there is a dose defect, as shown in FIGS. 10 and 11.

Since the major axis of the elliptically polarized light L2 is inclined as shown in FIG. 9 even in the non-defective shot in which there is no dose defect or focus defect, there is a tendency to think that the brightness in each non-defective shot will vary when the analyzer 42 is rotated so that the azimuth of the transmission axis of the analyzer 42 has an inclination angle of 90 degrees±3 degrees with respect to the transmission axis of the polarizer 32, and the two wafer images captured under each condition are compared. However, in the present embodiment, since the amount of illumination light is adjusted according to the state of the analyzer 42 so that the luminance is constant in the case of a non-defective shot (the reference shot described above), the brightness is the same in the two images for a non-defective shot.

Figure 7:
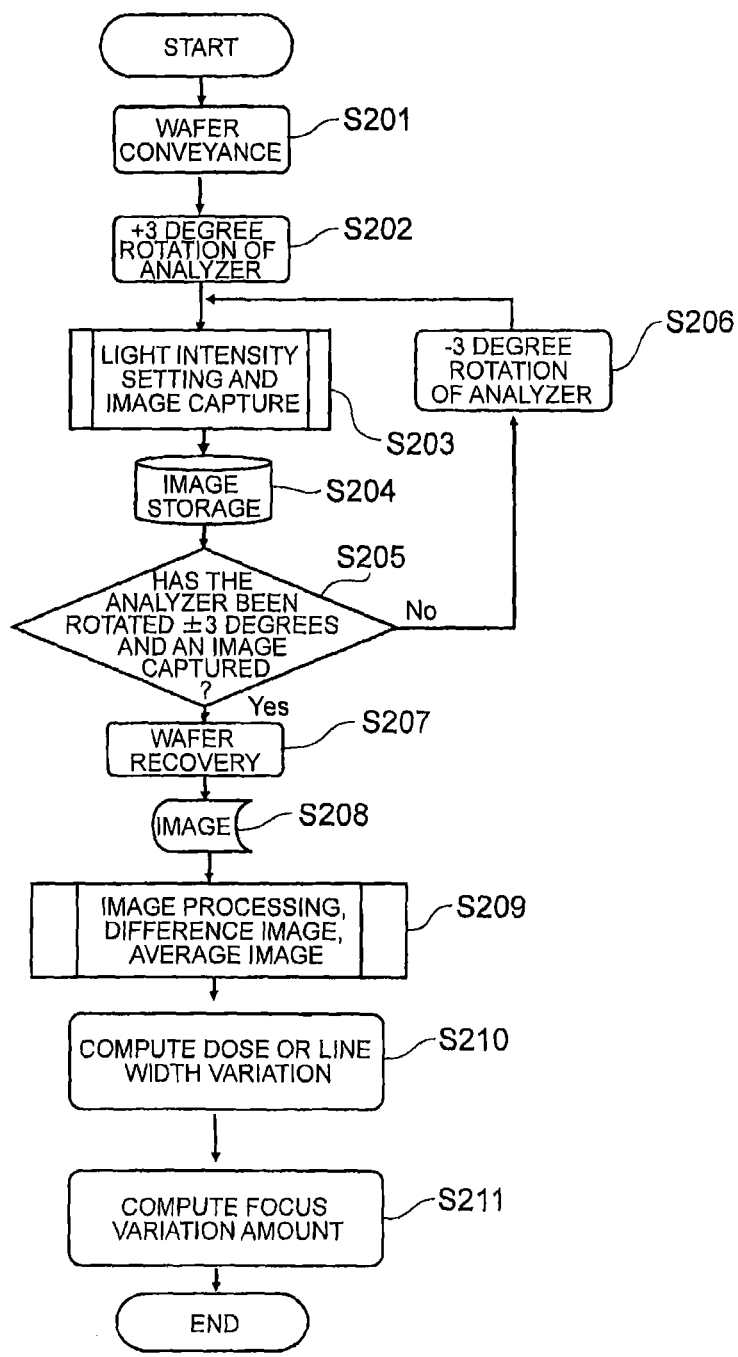
FIG. 7 is a flowchart showing the pattern evaluation method.

After a recipe is created (the coefficient K or the functions f and g are determined) in this manner, the repeating pattern 12 formed on the surface of the wafer 10 is evaluated (see FIG. 7). To evaluate the repeating pattern 12, the wafer 10 to be evaluated is first conveyed to the stage 20 (step S201). After the wafer 10 is conveyed, alignment is performed so that the direction of repetition of the repeating pattern 12 is inclined 45 degrees with respect to the illumination direction (propagation direction of the linearly polarized light L1 at the surface of the wafer 10). In a case in which the angle of alignment is 67.5 degrees or 22.5 degrees during recipe creation, the angle is adjusted accordingly.

After conveyance and alignment of the wafer 10, the analyzer 42 is rotated so that the azimuth of the transmission axis of the analyzer 42 has an inclination angle of 90 degrees+3 degrees (93 degrees) with respect to the transmission axis of the polarizer 32 (step S202). At this time, the angle formed by the direction of vibration in the plane perpendicular to the propagation direction of the linearly polarized light L1, and the direction of vibration in the plane perpendicular to the propagation direction of the second linearly polarized light L3, is set to 90 degrees+3 degrees (93 degrees).

The amount of illumination light is then adjusted according to the state of the analyzer 42 so that the luminance is constant in the case of a non-defective shot (the reference shot described above), the linearly polarized light L1 is radiated to the surface of the wafer 10, and the regularly reflected light (elliptically polarized light L2) reflected by the surface of the wafer 10 is detected and captured by the imaging camera 44 via the analyzer 42 (step S203). At this time, the light from the light source 31 is converted to linearly polarized light L1 via the polarizer 32 and the illumination lens 33 and radiated to the surface of the wafer 10. The regularly reflected light (elliptically polarized light L2) reflected by the surface of the wafer 10 is collected by the acceptance lens 41, the second linearly polarized light L3 is extracted by the analyzer 42 to form an image on the imaging surface of the imaging camera 44, and the imaging camera 44 photoelectrically converts the regularly reflected image of the wafer 10 formed on the imaging surface by the second linearly polarized light L3, generates an image signal, and outputs the image signal to the image processing unit 50.

When the image signal of the wafer 10 produced from the second linearly polarized light L3 is inputted to the image processing unit 50, the image signal is stored in the internal memory (not shown) of the image processing unit 50 (step S204).

A determination is then made as to whether the analyzer 42 has been rotated so that the azimuth of the transmission axis of the analyzer 42 has an inclination angle of 90 degrees±3 degrees with respect to the transmission axis of the polarizer 32, and the regularly reflected image of the wafer 10 has been captured under each condition (step S205). In a case in which the determination is "No," the process proceeds to step S206, and after the analyzer 42 is rotated so that the azimuth of the transmission axis of the analyzer 42 has an inclination angle of 90 degrees–3 degrees (87 degrees) with respect to the transmission axis of the polarizer 32, the imaging of step S203 and the image storage of step S204 are repeated, and the process returns to step S205. At this time, the angle formed by the direction of vibration in the plane perpendicular to the propagation direction of the linearly polarized light L1, and the direction of vibration in the plane perpendicular to the propagation direction of the second linearly polarized light L3 is set to 90 degrees–3 degrees (87 degrees).

Also at this time, the amount of illumination light is adjusted each time so that the luminance of the non-defective shot is constant, as described above. Two images are thereby stored having the same luminance value of the reference shot and different azimuths of the transmission axis of the analyzer 42.

In a case in which the determination in step S205 is "Yes," the process proceeds to step S207, and the wafer 10 is recovered. When the wafer 10 is recovered, the image processing unit 50 reads the two images acquired in the previous step from the internal memory (step S208), and uses image processing to calculate images (i.e., a difference image and an average image) which are based on a difference and average of the signal strength in the two read images (step S209). The difference image and average image are calculated in the same manner as during the recipe creation described above.

When the difference image and average image are calculated, the average value (i.e., the average value of the difference of the signal strength (luminance) in the two images) of the luminance (signal strength) is computed for each shot from the calculated difference image, and the line width variation caused by variation of the dose (exposure amount), or the variation amount (i.e., shape variation of the repeating pattern 12) from the correct value of the dose is calculated for each shot by using Equation (3) or (4) described above from the computed average value (step S210). The line width variation or variation of the dose calculated in this manner is displayed on the monitor 55 together with the difference image or two images of the wafer 10, and a dose defect is reported in a case in which the line width variation or the variation of the dose exceeds a predetermined threshold value.

The average value (i.e., average value of the average of the signal strength (luminance) in the two images) of the luminance (signal strength) is then computed for each shot from the calculated average image, the variation amount from the correct value of the focus, or the LER (i.e., shape variation of the repeating pattern 12) described hereinafter is calculated for each shot from the computed average value by using Equations (5) and (6) described above, and evaluation of the repeating pattern 12 is ended (step S211). The variation of the focus calculated in this manner is displayed on the monitor 55 together with the average image, and a focus defect is reported in a case in which the variation of the focus exceeds a predetermined threshold value.

Figure 12:
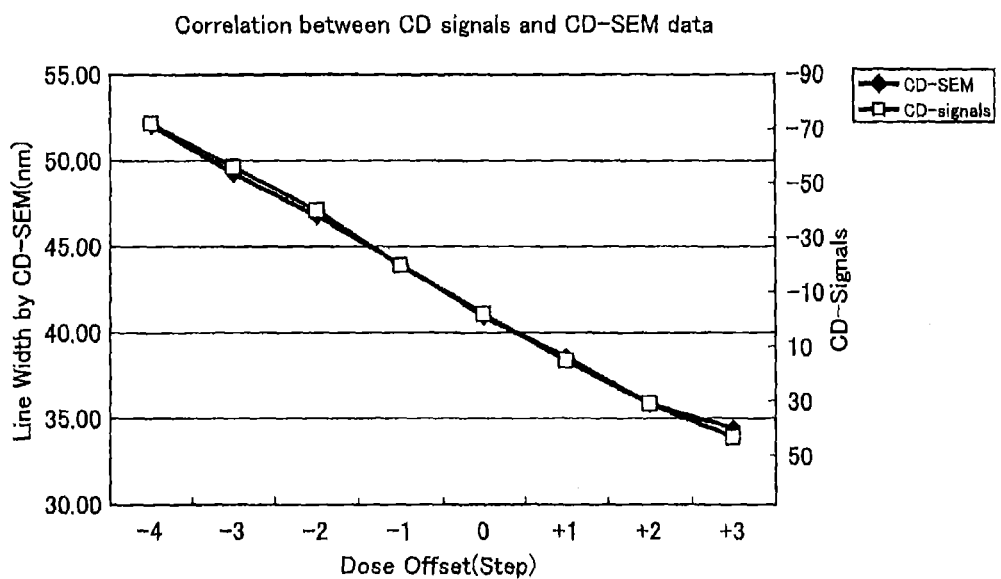
FIG. 12 is a graph showing the relationship between the line width variation and the dose variation.
Figure 13:
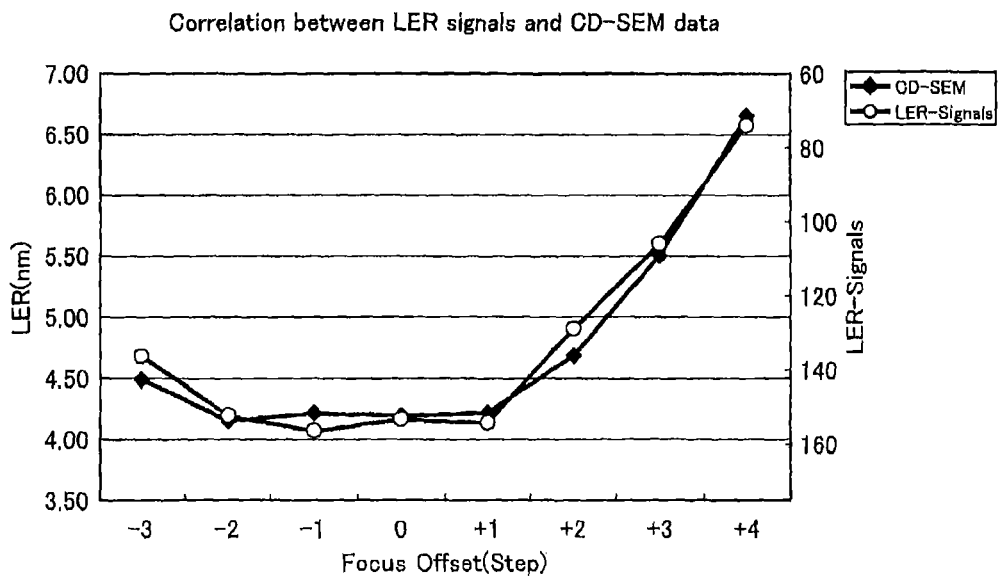
FIG. 13 is a graph showing the relationship between the LER and the focus variation.

FIG. 12 shows an example of data which show the correlation between the line width variation calculated by using Equation (3) from the difference of the signal strength in the two images, and the line width variation measured by scanning electron microscope (SEM). It is apparent from FIG. 12 that there is a high correlation between the computed values of the present embodiment and the measured values of SEM for the line width variation with respect to variation of the dose. FIG. 13 shows an example of data which show the correlation between the line edge roughness (LER) calculated by utilizing Equation (6) and other equations from the average of the signal strength in the two images, and the LER measured by SEM. It is apparent from FIG. 13 that there is a high correlation between the computed values of the present embodiment and the measured values of SEM for the variation in LER with respect to variation of the focus. The term "LER" herein refers to a value indicating the size of grooves/ridges formed on the wall surfaces of the pattern.

Through the evaluation device 1 and method of the present embodiment, by evaluating the shape of the repeating pattern 12 on the basis of two images of the wafer 10 captured under different conditions as to the angle between the direction of vibration of the linearly polarized light L1 and the direction of vibration of the second linearly polarized light L3, dose defects and focus defects can be distinguished and detected, and a cause of an abnormality in the repeating pattern 12 can be estimated (specified). Abnormalities in a pattern having a half pitch of 40 nm or 30 nm can also be detected and classified as dose defects or focus defects by using light such as H-line (wavelength λ=405 nm) light, for example, for which diffracted light is not generated.

At this time, by setting the angle formed by the direction of vibration in the plane perpendicular to the propagation direction of the linearly polarized light L1, and the direction of vibration in the plane perpendicular to the propagation direction of the second linearly polarized light L3 so as to be 90 degrees±3 degrees, the state (shape) of the repeating pattern 12 can be evaluated with high sensitivity.

Dose defects and focus defects can also be reliably distinguished and detected at this time by detecting the shape variation (line width variation or variation of the dose) of the repeating pattern 12 caused by variation of the dose (exposure amount) in the exposure device on the basis of the difference of the signal strength (luminance) in the two images of the wafer 10, and by detecting the shape variation (LER or variation of the focus) of the repeating pattern 12 caused by misalignment of the focus in the exposure device on the basis of the average of the signal strength (luminance) in the two images of the wafer 10. The effect of dose may also be considered when calculating the variation amount of the focus.

By radiating the linearly polarized light L1 so that the repeating pattern 12 has the same brightness in each of the two images of the wafer 10 in a case in which the repeating pattern 12 is normal (non-defective shot), the brightness of the normal repeating pattern 12 (non-defective shot) becomes constant, and erroneous detection of abnormalities (dose defects and focus defects) in the repeating pattern 12 can be prevented.

In the embodiment described above, the angle formed by the direction of vibration in the plane perpendicular to the propagation direction of the linearly polarized light L1, and the direction of vibration in the plane perpendicular to the propagation direction of the second linearly polarized light L3 is set to 90 degrees±3 degrees, but this configuration is not limiting. For example, a configuration may be adopted in which the stage 20 is rotated rather than the analyzer 42, the angle formed by the direction of vibration of the linearly polarized light L1 at the surface of the wafer 10 and the direction of repetition of the repeating pattern 12 are set so as to be 90 degrees apart from each other (e.g., 45 degrees and 135 degrees in the case of the present embodiment), and two images of the wafer 10 are taken under each condition. Through this configuration, in a case in which the repeating pattern 12 (wafer 10) is rotated 90 degrees with respect to the linearly polarized light L1, since the vertical positions of the graphs (average luminance) shown in FIGS. 10 and 11 are switched in relation to each other, the same effects as those described above can be obtained by calculating a difference image and average image and evaluating the repeating pattern 12 in the same manner as in the embodiment described above. The polarizer 32 and the analyzer 42 at this time are preferably in a crossed-Nicols state (a state in which the azimuth of the transmission axis of the analyzer 42 is inclined 90 degrees with respect to the transmission axis of the polarizer 32).

In the embodiment described above, a case is described in which a positive-type resist is used in the wafer 10, but this configuration is not limiting, and although tendencies are reversed in a case in which a negative-type resist is used, the present invention can be applied in the same manner. An off-axis elliptical mirror may also be used in at least one of the illumination system and the acceptance system (see the elliptical mirror of Japanese Laid-open Patent Publication No. 2006-135211, for example). The variation of the focus (shape variation of the repeating pattern 12) is also calculated based on the average image in the embodiment described above, but this configuration is not limiting, and because this average image is equivalent to an image of the wafer 10 in a crossed-Nicols state, the variation of the focus (shape variation of the repeating pattern 12) may also be calculated from the image of the wafer 10 in a crossed-Nicols state.

In the embodiment described above, the analyzer 42 is configured so that the azimuth of the transmission axis can be rotated about the optical axis of the acceptance system 40, through the use of the rotation drive device 43, but this configuration is not limiting, and a configuration may be adopted in which, for example, a ½ λ plate is disposed between the acceptance lens 41 and the analyzer 42, and the azimuth of the slow axis of the ½ λ plate is rotated about the optical axis of the acceptance system 40.

In the embodiment described above, a repeating pattern 12 formed on the surface of a wafer 10 is evaluated, but this configuration is not limiting, and it is also possible to evaluate a pattern formed on a glass substrate, for example.

EXPLANATION OF NUMERALS AND CHARACTERS

1: evaluation device
10: wafer (substrate)
12: repeating pattern
30: illumination system (illumination unit)
40: acceptance system
42: analyzer
43: rotation drive device (setting unit)
44: imaging camera (imaging unit)
50: image processing unit (evaluation unit)
L1: first linearly polarized light
L2: elliptically polarized light
L3: second linearly polarized light (polarization component)

The invention claimed is:

1. An evaluation device comprising:
an illumination system configured to radiate polarized light to a surface of a substrate having a pattern formed by using an exposure device; and
an evaluation unit configured to evaluate at least one of an exposure amount and a focusing state in exposure by an exposure device based on a polarization component of light from the surface of the substrate,
wherein the polarization component includes a first linear polarization component and a second linear polarization component which is different from the first linear polarization component.

2. The evaluation device according to claim 1, wherein the evaluation unit distinguishes and evaluates the exposure amount and the focusing state in exposure by an exposure device based on the polarization component of the light from the surface of the substrate.

3. The evaluation device according to claim 1, further comprising a light receiving system configured to extract the polarization component of the polarized light from the surface of the substrate, the evaluation unit evaluates the exposure amount and the focusing state in exposure by an exposure device based on the polarization component is extracted by the light receiving system.

4. The evaluation device according to claim 1, further comprising a light receiving system configured to extract the polarization component of the polarized light from the surface of the substrate,
wherein the light receiving system comprises:
an analyzer configured to set a plurality of transmission axis azimuths freely and to extract the first linear polarization component and the second linear polarization component; and
an imaging unit configured to capture an image of the substrate based on the first linear polarization component and an image of the substrate based on the second linear polarization component, the first and second linear polarization components being extracted by the analyzer.

5. The evaluation device according to claim 1, further comprising a light receiving system configured to extract the first linear polarization component of a first polarized light from the surface and the second linear polarization component of a second polarized light from the surface of the substrate,
wherein the evaluation unit evaluates the exposure amount and the focusing state of the exposure device based on the first linear polarization component and the second linear polarization component.

6. The evaluation device according to claim 5, wherein the light receiving system comprises,
an analyzer configured to set to a specified direction, and to extract the first linear polarization component and the second linear polarization component; and
an imaging unit configured to capture images of the substrate based on the first linear polarization component and the second linear polarization component, respectively.

7. The evaluation device according to claim 1, wherein
the illumination system comprises a light source and a polarizer configured to convert a light emitted from the light source to a linearly polarized light,
the polarizer is able to set a plurality of transmission axis azimuths freely, and
a polarization component of the linear polarized light emitted on the surface of the substrate can be changed by setting the transmission axis azimuth differently.

8. The evaluation device according to claim 5, further comprising a stage having a supporting surface to support the substrate, wherein the stage is rotatable around an axis perpendicular to the supporting surface.

9. The evaluation device according to claim 6, wherein the illumination system comprises a light source and a polarizer configured to convert a light emitted from the light source to a linearly polarized light, and
wherein the transmission axis azimuth of the analyzer and the transmission axis azimuth of the polarizer are perpendicular to each other.

10. The evaluation device according to claim 8, wherein
the illumination system comprises a light source and a polarizer configured to convert a light emitted from the light source to a linearly polarized light,
the light receiving system comprises,
an analyzer configured to set to a specified direction, and to extract the first linear polarization component and the second linear polarization component; and
an imaging unit configured to capture an image of the substrate based on the first linear polarization component and the second linear polarization component, respectively,
the transmission axis azimuth of the analyzer and the transmission axis azimuth of the polarizer being perpendicular to each other.

11. The evaluation device according to claim 1, wherein the illumination system radiates a linearly polarized light on the surface of the substrate.

12. The evaluation device according to claim 1, wherein the evaluation unit evaluates exposure amount and a focusing state of the exposure device based on the polarization component of light regularly reflected from the surface of the substrate upon the radiation of the polarized light by the illumination system.

13. An evaluation device comprising:
an illumination system configured to radiate polarized light to a surface of a substrate having a pattern formed by using an exposure device; and
an evaluation unit configured to evaluate at least one of a variation in a shape of the pattern caused by an exposure amount in exposure by an exposure device and a variation in a shape of the pattern caused by a focusing state in exposure by an exposure device based on a polarization component of light from the surface of the substrate,
wherein the polarization component includes a first linear polarization component and a second linear polarization component which is different from the first linear polarization component.

14. The evaluation device according to claim 13, wherein the evaluation unit distinguishes and evaluates the variation in the shape of the pattern caused by an exposure amount and the variation in the shape of the pattern caused by a focusing state based on the polarization component of the light from the surface of the substrate.

15. An evaluation method comprising:
radiating, using an illumination system, polarized light to a surface of a substrate having a pattern formed by using an exposure device; and
evaluating at least one of an exposure amount and a focusing state in exposure by an exposure device based on a polarization component of light from the surface of the substrate,
wherein the polarization component includes a first linear polarization component and a second linear polarization component which is different from the first linear polarization component.

16. The evaluation method according to claim 15, wherein the evaluating distinguishes and evaluates the exposure amount and the focusing state in exposure by an exposure device separately based on the polarization component of the light from the surface of the substrate.

17. The evaluation method according to claim 15, wherein the radiating radiates a linearly polarized light on the surface of the substrate.

18. The evaluation method according to claim 15, wherein the evaluating evaluates an exposure amount and a focusing state in exposure by an exposure device based on the polarization component of light regularly reflected from the surface of the substrate upon the radiation of the polarized light by the radiating.

19. An evaluation method comprising:
radiating, using an illumination system, polarized light to a surface of a substrate having a pattern formed by using an exposure device; and
evaluating at least one of a variation in a shape of the pattern caused by an exposure amount in exposure by an exposure device and a variation in a shape of the pattern caused by a focusing state in exposure by an exposure device based on a polarization component of light from the surface of the substrate,
wherein the polarization component includes a first linear polarization component and a second linear polarization component which is different from the first linear polarization component.

* * * * *

UNITED STATES PATENT AND TRADEMARK OFFICE
CERTIFICATE OF CORRECTION

| | | |
|---|---|---|
| PATENT NO. | : 8,705,034 B2 | Page 1 of 1 |
| APPLICATION NO. | : 13/676686 | |
| DATED | : April 22, 2014 | |
| INVENTOR(S) | : Fukazawa et al. | |

It is certified that error appears in the above-identified patent and that said Letters Patent is hereby corrected as shown below:

On the Title Page Item [60] (Related U.S. Application Data), Line 4, delete "Nov. 9, 2008." and insert -- Nov. 9, 2009. --, therefor.

In the Claims

Column 14, Line 12, in Claim 3, after "component" delete "is".

Signed and Sealed this
Twenty-second Day of July, 2014

Michelle K. Lee
*Deputy Director of the United States Patent and Trademark Office*